(12) United States Patent
Uzenbajakava et al.

(10) Patent No.: US 8,610,767 B2
(45) Date of Patent: Dec. 17, 2013

(54) APPARATUS FOR SKIN IMAGING, SYSTEM FOR SKIN ANALYSIS

(75) Inventors: Natallia Eduardauna Uzenbajakava, Eindhoven (NL); Sipke Wadman, Eindhoven (NL); Rachel Thilwind, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 382 days.

(21) Appl. No.: 12/922,710

(22) PCT Filed: Mar. 11, 2009

(86) PCT No.: PCT/IB2009/051015
§ 371 (c)(1),
(2), (4) Date: Sep. 15, 2010

(87) PCT Pub. No.: WO2009/115947
PCT Pub. Date: Sep. 24, 2009

(65) Prior Publication Data
US 2011/0013006 A1    Jan. 20, 2011

(30) Foreign Application Priority Data
Mar. 18, 2008 (EP) .................................. 08152936

(51) Int. Cl.
*H04N 7/18* (2006.01)
*A61B 5/00* (2006.01)

(52) U.S. Cl.
USPC .............................................. 348/77; 356/39

(58) Field of Classification Search
None
See application file for complete search history.

(56) References Cited

U.S. PATENT DOCUMENTS

| | | | |
|---|---|---|---|
| 5,241,369 A | 8/1993 | McNeil et al. | |
| 5,833,612 A | 11/1998 | Eckhouse et al. | |
| 7,872,754 B2 * | 1/2011 | Wadman | 356/445 |
| 7,978,332 B2 * | 7/2011 | Wadman | 356/446 |
| 8,077,319 B2 * | 12/2011 | Wadman | 356/446 |
| 2002/0080357 A1 | 6/2002 | Dana | |
| 2005/0010102 A1 | 1/2005 | Marchesini et al. | |
| 2007/0060819 A1 * | 3/2007 | Altshuler et al. | 600/475 |
| 2008/0146909 A1 * | 6/2008 | Abbink et al. | 600/407 |
| 2008/0319299 A1 * | 12/2008 | Stippick et al. | 600/407 |

FOREIGN PATENT DOCUMENTS

| | | | |
|---|---|---|---|
| WO | 0037923 A1 | 6/2000 | |
| WO | 2004077032 A1 | 9/2004 | |
| WO | 2007072403 A1 | 6/2007 | |
| WO | 2007119202 A1 | 10/2007 | |

\* cited by examiner

*Primary Examiner* — Jay Patel
*Assistant Examiner* — Reza Aghevli

(57) ABSTRACT

An apparatus for skin imaging uses a combination of near-field and far-field skin images under different angles of illumination. The apparatus provides a tool that may be employed for rapid screening of the skin for lesions that may be indicative of skin diseases, in particular skin cancers such as melanoma.

17 Claims, 1 Drawing Sheet

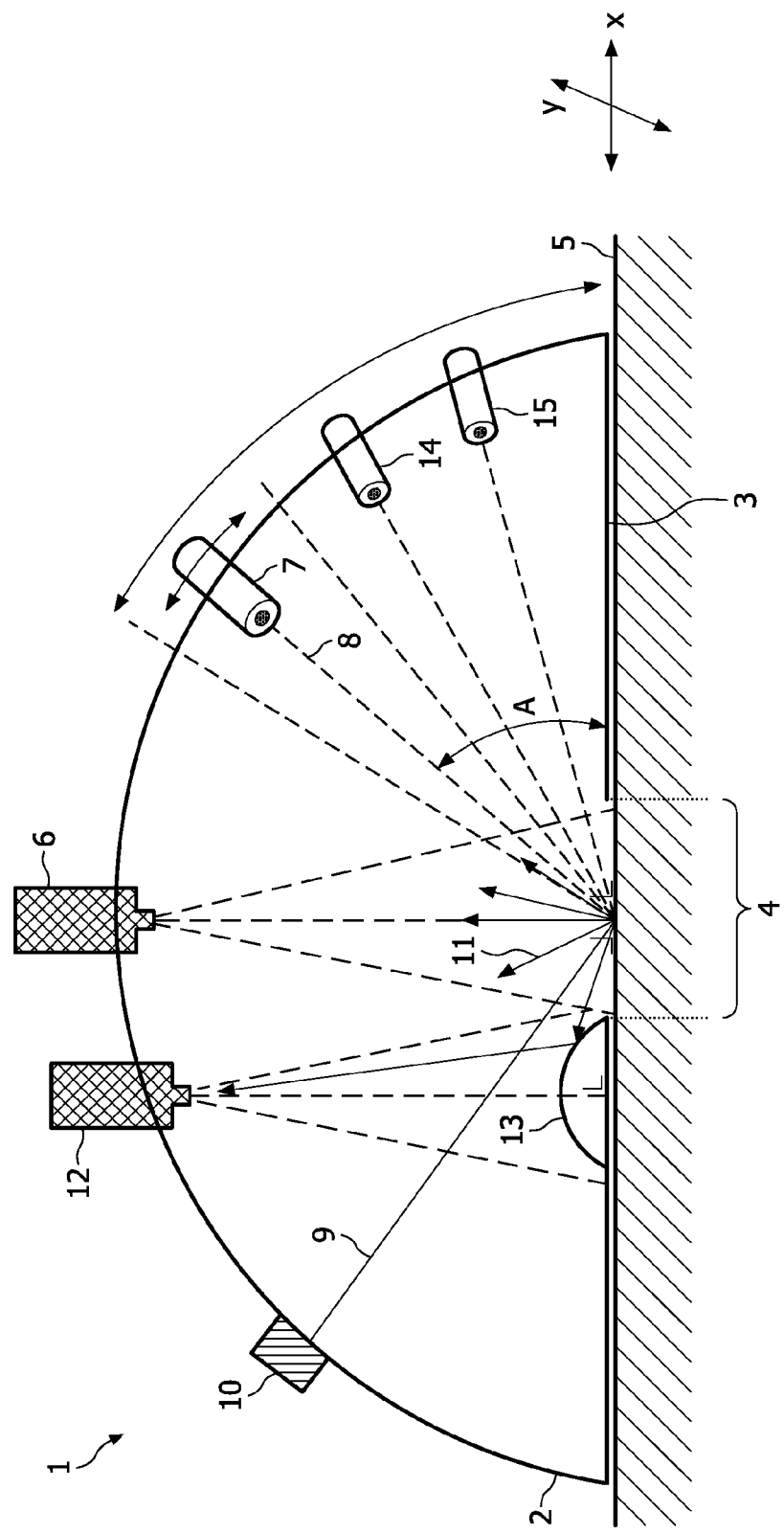

APPARATUS FOR SKIN IMAGING, SYSTEM FOR SKIN ANALYSIS

FIELD OF THE INVENTION

The invention relates to an apparatus for skin imaging, a system for skin analysis and a method for skin analysis.

BACKGROUND OF THE INVENTION

Melanoma is the most aggressive and the deadliest form of skin cancer. The annual occurrence and death are 60,000 and 7000 cases, respectively in the US only. When detected at an early stage, melanoma can be treated effectively at a relatively low cost of $ 1.8K, which results in high survival rate of 95%.

In contrast, progression of the disease in the late stage is associated with poor survival rate of less than 13% and dramatically increasing treatment costs of $60K per patient or higher. As a result, 88% of the total annual melanoma treatment costs is due to 18% of late stage cases.

At this moment, however, no official melanoma screening program exists. Currently, melanoma diagnosis is performed by general practitioner based on visual criteria. However, visual screening is very dependent on the skill and experience of the physician, and is generally prone to errors and overlooking of signals that may not be obvious at the early stages of the skin disease.

Available dermatological tools, e.g. a dermascope, are only useful in the hands of experienced dermatologists, who followed a dedicated training. Yet, there is a large spread in acquired data due to not reproducible data acquisition.

Thus, there is a long-felt need for improved skin analysis tools, providing easy and unambiguous analysis of the skin, allowing for reliable early detection of melanoma, as well as other skin cancer types and other skin diseases. Such a tool would provide easy and timely diagnosis, increasing survival rate and decreasing treatment costs.

It is an object of the invention to provide a diagnosis tool for the early detection of skin diseases, in particular skin cancer, more in particular melanoma.

SUMMARY OF THE INVENTION

The invention provides an apparatus for skin imaging, comprising a housing provided with a viewing window for positioning on a skin, at least one lighting means for lighting the viewing window from inside the housing, at least one near field image capturing means directed at the viewing window, at least one far field image capturing means directed at a reflector located adjacent to the viewing window, wherein the reflector is adapted for directing scattered diffuse light from the skin under the viewing window towards the far field image capturing means. With such an apparatus, it is possible to make reliable scans of skin that may be compared with reference data in order to detect changes and/or anomalies in specific locations of the skin. The housing is essentially light-free when the viewing window is placed on top of a skin area to be monitored. Preferably, the inner surface of the housing is provided with a coating with controlled optical properties that govern absorption, colour, scattering etc. The near field imaging means as well as the far field imaging means are preferably digital cameras. The near-field and far-field scattering are typically of different intensities. Therefore these cameras may operate under different optimal conditions. The reflector may comprise a single mirror or multiple mirrors. The viewing window may have various shapes, for instance circular or square.

Preferably, the near field imaging means are directed at the viewing windows essentially perpendicular to the skin surface. Thus, the near-field image is essentially a two-dimensional image with a maximum surface area exposed to the near-field camera.

In a preferred embodiment, the lighting means are directed at the skin surface under an oblique angle. An oblique angle is an angle that is not a multiple of 90 degrees; this implies that the incident angle with the skin surface is smaller than 90°.

The advantage of using multiple oblique angles is further elaborated in what follows. Using variable angles of incidence has two advantages. First, by varying the illumination angle, the position of the far-field scattering pattern on the inner surface of the housing is changed. This shift depends on tissue scattering coefficient, which is higher for malignant tissue. Analysing the change in the far-field images as a function of angle can provide information if the lesion is benign or malignant (cancer).

Second, using oblique incident angles has an impact on the penetration depth of the illuminating light. As a result, a selection can be made as to the depth to which, e.g., a tissue sample is probed, by adjusting the orientation of the optode(s). Therefore, information from different depth of the lesion can be obtained. This is especially important to a) detect skin cancer at an early stage, when its position is limited to the epidermal layer (approximately 70 to 100 micrometers below the skin surface) and b) to detect the depth of a cancer lesion at a late stage, where there is a high risk of metastases if a lesion reaches a blood-rich dermal layer of the skin.

It is advantageous if the lighting means are suitable for varying the incident angle. Thus, the near field and far field images may be recorded under different angles, which yield more information, and increases the sensitivity of the method. Some differences, changes or anomalies in the skin will not be as apparent under a single lighting angle: increasing the number of angles at which recordings are collected increases the chance of detecting anomalies.

Preferably, the lighting means are adapted to project a light pattern on the skin. Using an illumination pattern has the following advantages. First, it assists in obtaining 3-dimensional information about the shape of the object under investigation, i.e., a skin lesion. Malignant skin lesions may form a dome on top of the skin surface, which can be detected using 3-dimensional spatial information. Secondly, using an illumination pattern assists in obtaining information about light attenuation along an extended area. An illumination pattern may be achieved by providing the illumination means with a way to adjust the shape or pattern of the illuminated area within or near the field of view. The lighting means may comprise a single spot scanning an area of the skin in a predetermined pattern, or multiple combined spots at a given location, or multiple spots arranged in a predetermined a ring shape, or other appropriate shapes.

In a preferred embodiment, the lighting means are displaceable to vary the incident angle. This is a very reliable way of varying the incident angle of the light on the skin surface. Various mechanical displacement means are available to vary the angle in a reliable and reproducible way, for instance a motorized light source on tracks. A disadvantage is that it takes time to move the lighting source to a new location in between measurements, and moving parts are prone to defects.

In another preferred embodiment, the lighting means comprise multiple independently powered light sources positioned under different incident angles. These light sources may be addressed sequentially in order to vary the lighting angle. As the lighting angles are fixed, the reproducibility is very good. A disadvantage is that multiple light sources are needed that may be expensive.

In a preferred embodiment, the incident angles comprise at least one oblique angle.

Particularly useful oblique angles are from 20° to 75°, most preferably approximately 55°, as this is the approximate Brewster angle for human skin.

Preferably, the incident angles also comprise an angle of approximately 0°. The difference between the effect of light scattering on parameters of the near-field and far-field images at 0° and an oblique angle is often large, and thus the combination yields a lot of information.

It is advantageous if the lighting means comprise a polarized light source, preferably a laser or an unpolarised light source provided with a polarizing means. A polarized light source yield a more specific scattering pattern than non-polarized light.

In a preferred embodiment, the spectral composition emitted by the light source can be varied. Thus, measurements can further optimized, and carried out at various wavelengths, which further optimises the sensitivity of the measurement. Preferably but not necessarily, each measurement is done at a single wavelength.

It is preferred if the reflector is a convex surface of a predetermined shape, protruding from the housing. Such a reflector captures a wide area of scattered diffuse light, and thus provides a high density of information for the far field imaging means.

The invention also provides a system for skin analysis, comprising an apparatus including controlling means for controlling the lighting means and the imaging means, data processing means for processing images captured by the near field and far field image capturing means, and display means for displaying images and/or processed data. With such a system, it is relatively easy for a skilled person to gain insight in the current state of the skin of a person, and to notice changes in a skin when comparing analyzed images to images taken at an earlier stage, for instance weeks, months or years earlier. The analysis system according to the invention helps to indicate changes indicative of for instance skin diseases at an early change, typically earlier than possible even by experienced physicians. Upon the detection of possibly malign changes in the skin, the physician may decide to initiate further tests, for instance histological or microbiologic testing, that may lead to an early diagnosis of a skin disease. Early diagnosis of potentially lethal skin diseases such as melanoma improves the chances of survival for the patient.

The invention also provides a method for skin analysis, comprising the steps of positioning the viewing window of an apparatus according to the invention, as described above, on a skin area to be analysed, lighting at least part of the skin area by the lighting means under an incident angle, capturing at least one image of the lighted skin by the near field image capturing means, capturing at least one image as reflected by the reflector from the illuminated skin by the near field image capturing means, and comparing the captured images with reference images. Such a combination of near field and far field images under different lighting angles provides reliable and sensitive information, and developing changes in the analyzed skin are likely to be noticed. In contrast, if only a near field or a far field would be taken, some changes are less likely to be noticed at an early stage. Also, the angle or the pattern of the lighting has a great influence on the image created, and may increase the chance skin lesions are noticeable. The obtained images may be further subjected to images segmentation and pattern recognition analysis and classifying lesions, preferably on an automated system. Illumination of the skin can be done with a light source partially outside the dome shaped screen from a distance or in proximity from the edge of the skin aperture.

The method may further include the positioning of the viewing window of an apparatus according to the invention on a skin area to be analysed.

The method may further include the acquiring of far-field images of the skin distant from a suspicious lesion, preferably at 0° and at various oblique angles. The images taken at a distance from the suspicious lesion may then be used as a standard, which is particularly if no historical data is available.

Advantageously, it is possible to determine a "center-of-gravity" for each image and shift in the "center-of-gravity" depending on the angle. It is then possible to acquire far-field images of the suspicious lesion (possibly malignant) at 0° and an oblique angle, and estimate a "center-of-gravity" for each image and shift in the "center-of-gravity" depending on the angle. For comparison, it is also useful to acquire far-field images of a mole (a non-malignant lesion) at 0° and an oblique angle, estimating a "center-of-gravity" for each image and shift in the "center-of-gravity" depending on the angle. This then enables the comparison of the difference in the shifts in the "center-of-gravity" in the images of the skin, moles, and suspicious lesion, which makes it relatively easy for a skilled person to assess if the suspicious lesion is indeed malignant.

Preferably, a plurality of images is taken under varying incident angles of lighting. This increases the chance of detecting skin lesions. Preferably, a plurality of images is taken under varying incident angles ranging from 0° to at least 75°. By using high incident angles, more superficial layers of the skin can be assessed. This is beneficial for detecting a cancer lesion at an early stage, since it is known that is starts from the epidermal layer, which is approximately 70 to 100 micrometers deep in the skin.

Most preferably, the plurality of images comprises images taken at least a first angle between 15° and 25°, and a second angle between 55° and 65°. It is preferred if the incident angles comprise at least 0° and at least one oblique angle, and preferably the angles include the Brewster angle of fully polarised reflection

BRIEF DESCRIPTION OF THE DRAWINGS

FIG. 1 shows an apparatus according to the invention.

DETAILED DESCRIPTION OF EMBODIMENTS

FIG. 1 shows an apparatus 1, comprising a light-free housing 2 that can comprise a whole or part of a hemisphere. A bottom plate 3 of the housing 1 is provided with a window opening 4, which is placed on top of a skin area 5 to be examined. The skin 5 forms an approximately flat surface in the window location. A device may include additional means to control pressure or force exerted on the skin. This is to minimize skin deformation, skin fluid displacement and the related effects, which may affect the measurements. The window 4 may be open, but can also be provided with an essentially flat, sufficiently transparent material layer, preferably a glass plate, most preferably a reflection-free glass plate. When no glass plate is used, it is preferred if the monitored part of the skin 5 is as flat as possible. This may be achieved by keeping the scanned area sufficiently small, or by using skin stretching means. Immersion fluid (known from microscopy) may be applied on the skin between the skin and the exit window of the device. This minimizes the specular reflectance from the skin surface, increases light penetration in the skin, and maximizes light collection efficacy. Perpendicular to the skin surface 5, a first, near-field imaging camera 6 is positioned above the window opening 4. Under an angle A, a light source 7 is directed at the exposed skin area 4. Part of the light 8 is absorbed by the skin 5, another part is reflected and yet another part is scattered. When a glass plate is used in the window 4, the maximum angle that can be used is typically 75° (depending on the type of glass), as at higher angles typically no useful data can be obtained due to total internal reflection. The reflected light 9 may be captured by a light trap 10, in order to prevent further scattering within the housing. Part of the scattered light 11 is recorded directly by the first camera 6. The first camera records near-field scattered light, which is scattered under angles smaller than 90° with respect to the incident beam 8, and has a relatively high intensity. Another part of the scattered light 11 is reflected towards a second, far-field, imaging camera 12, through a suitably curved mirror 13 located adjacent to the opening 4. The indirectly reflected far-field scattering is scattered under angles greater than 90° with respect to the incident beam 8, and has a relatively low intensity. As the far-field camera 12 is separated from the near-field image camera 6, each camera can be easily optimised with respect to the intensity as recorded, for an optimal signal-to-noise ratio.

The angle A under which the light source 7 lights the skin 5 can be varied, either through mechanical movement of the laser, or through adjustable optics such as mirrors, or by using an optical fiber to deliver light from a remote light source, which position and angle can be displaced with respect to the skin. Alternatively, a number of additional lasers 14, 15 (or other light sources) can be positioned under fixed angles A, an operated sequentially in order to achieve the same illumination conditions that could be achieved by moving a single laser 7.

By recording both the near-field image 6 and the far-field image 12 under different incident laser angles A. Images at numerous angles could be measured, however, this would lead to enormous amounts of data. In practice, it is preferred to record under a limited amount of angles, preferably from 3 to 10 angles per skin position. A particularly useful data set could for instance be obtained by measuring at angles of approximately 0°, 20°, 40°, 55° and 75°. The apparatus can then be moved towards different locations on the skin in both the X and Y directions, preferably by automated means. Thus, a specific part of the skin can be scanned at a desired resolution, and the data can be processed. The scanning of a specific skin area may be done relatively fast.

The processed combination of near-field and far-field images under different angles yields a skin profile. The recorded images may be compared with reference images, for instance images that were recorded at an earlier time, or a recording of a healthy part of the skin. This method yields a reliable and easy way of indicating anomalies and/or changes in the skin, which can be a great help in diagnosing for instance skin cancer. As the method is very sensitive, such skin diseases are more likely to be detected at an earlier stage than known methods. Early detection is in particular of importance in the case of skin cancers. Combined with automated data processing system and decision support this provides a basis for easy-to-access tool for skin cancer screening.

The apparatus 1 can be operated by a person who does not need a full medical education, nor experience. The collected image data and/or analysis data may be sent to a skilled person, or there may be a pre-selection of potentially harmful developments by a relatively un-skilled person that need to be looked at by a higher qualified expert. Once an alarming difference in images is noted, the examined person can be forwarded to clinicians, who may carry out a full diagnosis in order to confirm the development of a certain disease such as melanoma. Thus, the limited time available to skilled professionals can be used more effectively, while at the same time, a larger amount of persons can be monitored for potentially hazardous skin diseases.

Although the application for early detection of skin diseases is considered to be the most important application of the apparatus 1 according to the invention, it may also be used for other applications, for instance cosmetic applications such as measurement of skin type, monitoring of pigment disorders, e.g., age spots and vitiligo.

The invention claimed is:

1. An apparatus for skin imaging, comprising:
   a housing having a housing surface provided with a viewing window for positioning on a skin surface;
   at least one light unit configured to emit light towards the viewing window from inside the housing;
   at least one near field imager directed at the viewing window; and
   at least one far field imager directed at a reflector located adjacent to the viewing window,
   wherein the reflector is located on the housing surface, and
   wherein the reflector is configured to direct scattered diffuse light from the skin under the viewing window towards the far field imager.

2. The apparatus according to claim 1, wherein the near field imaging unit is directed essentially perpendicular to the skin surface.

3. The apparatus according to claim 1, wherein the light unit is further configured to vary an angle that the light is incident on the viewing window.

4. The apparatus according to claim 3, wherein the light unit is displaceable to vary the angle.

5. The apparatus according to claim 3, wherein the light unit comprises multiple independently powered light sources positioned under different angles.

6. The apparatus according to claim 1, wherein the wherein the light unit is configured to project a light pattern on the skin.

7. The apparatus according to claim 1, wherein an angle that the light is incident on the viewing window between the housing surface that includes the viewing window and the light comprises at least one oblique angle.

8. The apparatus according to claim 7, wherein the oblique angle is from 20° to 75°.

9. The apparatus according to claim 3, wherein the angle is between the housing surface that includes the viewing window and the light, and wherein the angle comprise an oblique angle as well as an angle of approximately 0°.

10. The apparatus according to claim 1, wherein the light unit comprises a polarized light source.

11. The apparatus according to claim 1, wherein the light unit is tunable to emit light having a desired wavelength.

12. The apparatus according to claim 1, wherein the reflector is a convex mirror of a predetermined shape, protruding from the housing surface towards the inside of the housing.

13. A system for skin analysis comprising:
    an apparatus, wherein the apparatus includes:
    a housing having a housing surface provided with a viewing window for positioning on a skin surface:
    at least one light unit configured to light the viewing window from inside the housing;
    a near field imager directed at the viewing window; and
    a far field imager directed at a reflector located adjacent to the viewing window, wherein the reflector is located on the housing surface, and wherein the reflector is configured to direct scattered diffuse light from the skin under the viewing window towards the far field imager;

a controller configured to control the at least one light unit, the near field imager and the far field imager;

a processor configured to process at least one of data and images captured by the near field imager and the far field imager; and a display configured to display the at least one of data and images.

14. A method for skin analysis, comprising the steps of:

positioning the viewing window of an apparatus on a skin area to be analyzed, wherein the apparatus includes:

a housing having a housing surface provided with a viewing window for positioning on a skin surface;

at least one light unit configured to emit light towards the viewing window from inside the housing;

at least one near field imager directed at the viewing window; and at least one far field imager directed at a reflector located adjacent to the viewing window, wherein the reflector is located on the housing surface, and wherein the reflector is configured to direct scattered diffuse light from the skin under the viewing window towards the far field imager;

lighting at least part of the skin area by the at least one light unit under an incident angle;

capturing at least one image of the lighted skin area by the near field imager;

capturing at least one image as reflected by the reflector from the lighted skin area by the far field imager; and comparing the captured images with reference images.

15. The method for skin analysis according to claim 14, wherein a plurality of images is captured under varying incident angles of lighting.

16. The method according to claim 15, wherein the incident angles comprise at least 0° and at least one oblique angle.

17. The apparatus of claim 1, wherein the light unit comprises a laser.

* * * * *